US009375389B2

(12) United States Patent
Jiang et al.

(10) Patent No.: US 9,375,389 B2
(45) Date of Patent: *Jun. 28, 2016

(54) PERSONAL CARE COMPOSITIONS CONTAINING ZINC PYRITHIONE AND A METAL-PHOSPHONATE COMPLEX

(71) Applicant: The Procter & Gamble Company, Cincinnati, OH (US)

(72) Inventors: Chunpeng Jiang, Beijing (CN); Zhe Liu, Beijing (CN); Juan Wang, Beijing (CN); Xiujun Xu, Beijing (CN); Karl Shiqing Wei, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,714

(22) Filed: Apr. 17, 2014

(65) Prior Publication Data

US 2014/0315875 A1  Oct. 23, 2014

(30) Foreign Application Priority Data

Apr. 18, 2013  (CN) .............................. 2013-074366
Feb. 28, 2014  (CN) .............................. 2014-072729

(51) Int. Cl.
| | | |
|---|---|---|
| *A61K 8/02* | (2006.01) | |
| *A61K 8/27* | (2006.01) | |
| *A01N 43/40* | (2006.01) | |
| *A61K 8/49* | (2006.01) | |
| *A61K 8/55* | (2006.01) | |
| *A61Q 19/10* | (2006.01) | |
| *C11D 7/36* | (2006.01) | |
| *C11D 3/28* | (2006.01) | |
| *C11D 3/34* | (2006.01) | |
| *C11D 3/36* | (2006.01) | |
| *C11D 3/48* | (2006.01) | |
| *C11D 17/00* | (2006.01) | |
| *A61Q 17/00* | (2006.01) | |

(52) U.S. Cl.
CPC . *A61K 8/27* (2013.01); *A01N 43/40* (2013.01); *A61K 8/4933* (2013.01); *A61K 8/55* (2013.01); *A61Q 17/005* (2013.01); *A61Q 19/10* (2013.01); *C11D 3/28* (2013.01); *C11D 3/3427* (2013.01); *C11D 3/361* (2013.01); *C11D 3/48* (2013.01); *C11D 7/36* (2013.01); *C11D 17/0047* (2013.01); *A61K 2800/51* (2013.01); *A61K 2800/58* (2013.01)

(58) Field of Classification Search
CPC ..... A61K 8/4933; A61K 8/58; A61K 8/0216; A61Q 17/005; A61Q 19/10
USPC ....................................................... 424/401
See application file for complete search history.

(56) References Cited

U.S. PATENT DOCUMENTS

| | | |
|---|---|---|
| 2,809,971 A | 10/1957 | Bernstein et al. |
| 3,235,455 A | 2/1966 | Judge et al. |
| 3,281,366 A | 10/1966 | Judge et al. |
| 3,412,033 A | 11/1968 | Karsten |
| 3,725,547 A | 4/1973 | Kooistra |
| 4,161,526 A | 7/1979 | Gorman |
| 4,205,062 A | 5/1980 | Daahn |
| 4,345,080 A | 8/1982 | Bolich, Jr. |
| 4,379,753 A | 4/1983 | Bolich, Jr. |
| 4,482,715 A | 11/1984 | Trotz |
| 4,533,736 A | 8/1985 | Trotz |
| 4,565,693 A | 1/1986 | Marschner |
| 4,708,863 A | 11/1987 | Bews et al. |
| 4,714,563 A | 12/1987 | Kajs |
| 4,818,436 A | 4/1989 | French |
| 4,935,061 A | 6/1990 | French |
| 4,957,658 A | 9/1990 | French |
| 5,037,818 A | 8/1991 | Sime |
| 5,104,645 A | 4/1992 | Cardin et al. |
| 5,198,140 A | 3/1993 | Joshi et al. |
| 5,540,860 A | 7/1996 | Hosseini et al. |
| 5,562,995 A | 10/1996 | Kappock et al. |
| 5,573,699 A | 11/1996 | Jones et al. |
| 5,612,301 A | 3/1997 | Inman |
| 5,714,447 A | 2/1998 | Jones et al. |
| 5,883,154 A | 3/1999 | Kappock et al. |
| 5,886,031 A | 3/1999 | Shin et al. |
| 5,972,920 A | 10/1999 | Seidel |
| 6,015,547 A | 1/2000 | Yam |
| 6,017,562 A | 1/2000 | Kaufman et al. |
| 6,017,936 A | 1/2000 | Polson et al. |
| 6,096,122 A | 8/2000 | Kappock |
| 6,096,297 A | 8/2000 | Jones et al. |
| 6,162,446 A | 12/2000 | Hani et al. |

(Continued)

FOREIGN PATENT DOCUMENTS

| | | |
|---|---|---|
| EP | 0034385 A2 | 8/1981 |
| EP | 0093541 A2 | 11/1983 |

(Continued)

OTHER PUBLICATIONS

"The stability of 2-pyridinethiol-1-oxide, sodium salt, as a function of pH", Robert J. Fenn et al, J. Soc. Cosmet. Chem., 33, 243-248 (Aug. 1982).
"Effect of Premicellar Aggregation on the pKa of Fatty Acid Soap Solutions", J.R. Kanicky et al., Langmuir 2003, 19, 2034-2038, 2003 American Chemical Society, Published on Web Feb. 7, 2003.
"Chromatographic Behavior of Pyrithiones", Caren Anja Doose et al., Journal of Chromatography A, 1052 (2004) 103-110.
"Effect of Degree, Type, and Position of Unsaturation on the pKa of Long-Chain Fatty Acids", James R. Kanicky et al, Journal of Colloid and Interface Science 256, 201-207 (2002).
PCT International Search Report and Written Opinion for PCT/US2012/026880, dated May 29, 2012.
PCT International Search Report and Written Opinion for PCT/CN2014/072729, dated May 28, 2014.
U.S. Appl. No. 13/856,457, filed May 22, 2013, Cook et al.
U.S. Appl. No. 14/208,821, filed Mar. 14, 2014, Smith, III et al.

(Continued)

*Primary Examiner* — Shirley V Gembeh

(57) ABSTRACT

The present invention relates to an antimicrobial bar soap that contains zinc pyrithione and a metal-phosphonate complex and is characterized by enhanced discoloration resistance, extended shelf life and/or increased anti-microbial efficacy.

25 Claims, 3 Drawing Sheets

(56) References Cited

U.S. PATENT DOCUMENTS

| | | |
|---|---|---|
| 6,242,007 B1 | 6/2001 | Mohseni et al. |
| 6,277,360 B1 | 8/2001 | Carew et al. |
| 6,432,432 B1 | 8/2002 | Mohseni et al. |
| 6,451,300 B1 | 9/2002 | Dunlop et al. |
| 6,465,015 B1 | 10/2002 | Mohseni et al. |
| 6,649,155 B1 | 11/2003 | Dunlop et al. |
| 6,673,756 B2 | 1/2004 | Sonnenberg et al. |
| 6,682,724 B2 | 1/2004 | Mohseni et al. |
| 6,887,859 B2 | 5/2005 | Clapp et al. |
| 6,974,569 B2 | 12/2005 | Dunlop et al. |
| 7,026,308 B1 | 4/2006 | Gavin et al. |
| 7,381,415 B2 | 6/2008 | Yokoyama et al. |
| 7,544,367 B2 | 6/2009 | Mohseni et al. |
| 7,674,785 B2 | 3/2010 | Gavin et al. |
| 8,119,168 B2 | 2/2012 | Johnson et al. |
| 8,491,877 B2 | 7/2013 | Schwartz et al. |
| 2002/0001605 A1 | 1/2002 | Carew |
| 2004/0058855 A1 | 3/2004 | Schwartz |
| 2004/0161435 A1 | 8/2004 | Gupta |
| 2004/0186030 A1 | 9/2004 | Hofrichter |
| 2004/0191331 A1 | 9/2004 | Schwartz et al. |
| 2004/0213751 A1 | 10/2004 | Schwartz et al. |
| 2005/0118276 A1 | 6/2005 | Lei et al. |
| 2005/0244352 A1 | 11/2005 | Lemoine et al. |
| 2007/0009463 A1 | 1/2007 | Niebauer et al. |
| 2007/0128147 A1 | 6/2007 | Schwartz et al. |
| 2007/0190177 A1 | 8/2007 | Kling et al. |
| 2008/0063618 A1 | 3/2008 | Johnson et al. |
| 2008/0138442 A1 | 6/2008 | Johnson et al. |
| 2008/0160093 A1 | 7/2008 | Schwartz et al. |
| 2008/0206355 A1 | 8/2008 | Schwartz et al. |
| 2008/0249136 A1 | 10/2008 | Annis et al. |
| 2011/0039469 A1 | 2/2011 | Cabell et al. |
| 2011/0197906 A1 | 8/2011 | Schwartz |
| 2011/0197907 A1 | 8/2011 | Schwartz |
| 2011/0200649 A1 | 8/2011 | Schwartz |
| 2011/0200650 A1 | 8/2011 | Schwartz |
| 2011/0201588 A1 | 8/2011 | Schwartz |
| 2012/0039966 A1 | 2/2012 | Capretta et al. |
| 2012/0103151 A1 | 5/2012 | Jones et al. |
| 2012/0216408 A1 | 8/2012 | Cook et al. |
| 2012/0219610 A1 | 8/2012 | Smith, III et al. |
| 2012/0220516 A1 | 8/2012 | Smith |
| 2012/0246851 A1 | 10/2012 | Smith, III et al. |
| 2012/0324736 A1 | 12/2012 | Eagleton |
| 2013/0042482 A1 | 2/2013 | Bradford et al. |
| 2013/0045248 A1 | 2/2013 | Coffindaffer et al. |
| 2013/0045255 A1 | 2/2013 | Smith, III et al. |
| 2013/0045256 A1 | 2/2013 | Schwartz |
| 2013/0045257 A1 | 2/2013 | Alwattari et al. |
| 2013/0045263 A1 | 2/2013 | Smith, III et al. |
| 2013/0045284 A1 | 2/2013 | Stella |
| 2013/0045285 A1 | 2/2013 | Stella et al. |
| 2013/0045907 A1 | 2/2013 | Lanzalaco et al. |
| 2013/0045961 A1 | 2/2013 | Smith, III et al. |
| 2013/0048005 A1 | 2/2013 | Smith, III et al. |
| 2013/0205959 A1 | 8/2013 | Jones et al. |
| 2013/0222057 A1 | 8/2013 | Henshaw |
| 2013/0280200 A1 | 10/2013 | Schwartz |

FOREIGN PATENT DOCUMENTS

| | | |
|---|---|---|
| EP | 0158481 A2 | 10/1985 |
| EP | 0196824 A2 | 10/1986 |
| EP | 0217635 A2 | 4/1987 |
| EP | 0285388 A2 | 10/1988 |
| EP | 0468564 A2 | 1/1992 |
| JP | 2001-278863 A | 10/2001 |
| JP | 2006-176675 | 12/2004 |
| WO | 94/14408 A1 | 7/1994 |
| WO | 94/14409 A1 | 7/1994 |
| WO | 99/66886 A1 | 12/1999 |
| WO | 00/35413 A1 | 6/2000 |
| WO | 02/00178 A1 | 1/2002 |
| WO | 2006/110386 A1 | 10/2006 |
| WO | 2011/147941 A1 | 12/2011 |
| WO | 2012/058557 A2 | 5/2012 |
| WO | 2012/116466 A1 | 9/2012 |

OTHER PUBLICATIONS

U.S. Appl. No. 13/890,369, filed May 9, 2013, Smith, III et al.
PCT International Search Report and Written Opinion of the International Searching Authority for PCT/CN2014/072729 dated May 28, 2014, 13 pages.
Supplementary International Search Report for PCT/CN2014/072729 dated Jul. 21, 2015, 7 pages.
Head & Shoulders 2 in 1 Anti-Dandruff Shampoo, Mintel GNPD database, Record ID: 989270, XP-002741664, Oct. 2008.
Persavon Bebe Fabric Detergent, Mintel GNPD database, Record ID: 1543037, XP-002741665, May 2011.

US 9,375,389 B2

PERSONAL CARE COMPOSITIONS CONTAINING ZINC PYRITHIONE AND A METAL-PHOSPHONATE COMPLEX

FIELD OF THE INVENTION

The present invention relates to personal cleansing compositions, more specifically bar soap compositions, comprising zinc pyrithione and a metal-phosphonate complex with enhanced discoloration resistance, extended shelf life, and/or increased anti-microbial efficacy.

BACKGROUND OF THE INVENTION

Pyrithione (also known as 1-Hydroxy-2-pyridinethione, 2-pyridinethiol-1-oxide, 2-mercaptopyridine-N-oxide, pyridine-2-thione-N-oxide, pyridinethione-N-oxide, 2-pyridinethione, pyridinethione, or simply "PT") has been noted for its bactericidal and fungicidal activities. Pyrithione is a bidentate ligand that forms stable complexes with most transitional metals. Metallization of pyrithione often results in highly augmented biocidial activities. Metal salts of pyrithione, such as for example, sodium pyrithione, magnesium pyrithione, barium pyrithione, bismuth pyrithione, strontium pyrithione, copper pyrithione, zinc pyrithione, cadmium pyrithione, and zirconium pyrithione, are widely used as fungicides and bactericides in a broad spectrum of commercial products, such as metalworking fluids, lubricants, paints, cosmetics and toiletries.

Zinc pyrithione (or "ZPT") is especially useful as a broad-spectrum anti-microbial agent and preservative. It is active against both gram-positive and gram-negative bacteria, as well as fungi and yeasts. Therefore, ZPT has been used in various personal care compositions, such as for example, anti-dandruff shampoos, hair conditioners, leave-on tonics, and anti-microbial foot powders.

Bar soap is a popular product form for cleansing. A bar soap comprising ZPT is particularly desirable for its broad-spectrum antimicrobial efficacy. Aesthetics of consumer products such as bar soaps have significant impact on the consumers' perception of the products, which will in turn determine the acceptability of the products by the consumers. However, pyrithione-containing compounds can become discolored in the presence of ferric or cupric ions, even if the ferric irons are present only in trace amounts. The presence of such a color change is typically referred to as "discoloration" (usually to gray, green, blue or purple colors) and is believed to be due to the formation of a dark colored pyrithione precipitate compound from the reaction of the pyrithione groups with unwanted ferric (iron) or cupric ions that are found in the metal parts of the abovementioned manufacturing equipment. The metal ions can also be introduced into the soap compositions unintentionally as impurities in the raw materials used for making bar soap. Further, during manufacturing, handling or storage, various metallic parts of the manufacturing equipment, such as roller mills, pipes, or nozzles, may come into contact with the soap noodles or pellets, thereby introducing metal ions into the soap composition. In some situation, such contact can be maintained for a long time (e.g. overnight to 24 hours), and at a relatively elevated temperature, thereby increasing interaction between ZPT and metal ions.

The resultant discoloration may adversely affect the overall aesthetics of the bar soaps and give consumers a negative impression of the soap quality.

In the past, a number of solutions have been developed in attempt to solve the ZPT discoloration problem. For example, in U.S. Pat. Nos. 4,161,526 and 5,883,154, zinc salts (such as zinc acetate, zinc chloride and zinc sulfate), zinc hydroxide and zinc oxide have been used to address the ZPT discoloration problem. In U.S. Pat. Nos. 4,818,436, 4,957,658 and 4,533,736, 1-hydroxyethane-1,1-diphosphonic acid (HEDP), borate or sulfite has been used to reduce ZPT discoloration.

However, none of these solutions can completely eliminate or effectively reduce the undesirable discoloration in ZPT-containing bar soaps, which remains as a continuing concern for manufacturers, and more importantly, they can also lead to noticeable degradation of ZPT in the bar soaps. ZPT has been known to be unstable when solubilized. It may undergo transformation upon exposure to oxidizing species or certain metal cations, such as $Cu^{2+}$ and $Fe^{3+}$. The presence of the above-mentioned compounds in bar soap compositions further aggravates ZPT instability and results in significant ZPT loss over time, which in turn reduces the anti-microbial effect of ZPT-based bar soap compositions.

There is therefore a continuing need for improved ZPT-based anti-microbial bar soap products with improved discoloration resistance for more pleasing product aesthetics and better consumer appeal, as well as enhanced ZPT stability for extended shelf life of the products.

SUMMARY OF THE INVENTION

The present invention relates to a personal cleansing composition containing: (a) from about 0.01% to about 5% by weight of ZPT, (b) from about 0.01% to about 10% by weight of a metal-phosphonate complex, which comprises one or more phosphonate chelants coordinately bonded to one or more metal ions, and (c) from about 20% to about 95% by weight of at least one surfactant. Such a personal cleansing composition is preferably in the form of a bar soap. Further, it is preferably characterized by a pH value ranging from about 9.9 to about 10.7 when dispersed in a 1 wt % aqueous solution.

In another aspect, the present invention relates to a method for forming a bar soap, which includes the steps of: (a) preparing a mixture containing about 0.01% to about 5% of ZPT, from about 0.01% to about 10% of the above-described metal-phosphonate complex, and from about 20% to about 95% of at least one surfactant by total weight of said mixture; and (b) shaping the mixture to form a bar soap. The bar soap so formed preferably has a pH value ranging from about 9.9 to about 10.7 when dispersed in a 1 wt % aqueous solution.

In an embodiment, the metal in the metal-phosphonate complex may be selected from the group consisting of iron, copper and zinc. In a preferred but non-limiting embodiment of the present invention, the Zn-phosphonate complex are pre-formed by combining a phosphonate chelant with zinc oxide or a soluble zinc salt and then mixed with ZPT and the surfactant. In an alternative embodiment, the Zn-phosphonate complex are formed in situ by directly combining the phosphonate chelant, zinc oxide or a soluble zinc salt, ZPT and the surfactant.

These and other aspects of the present invention will become more apparent upon reading the following drawings and detailed description of the invention.

DETAILED DESCRIPTION OF THE INVENTION

Figure 1:
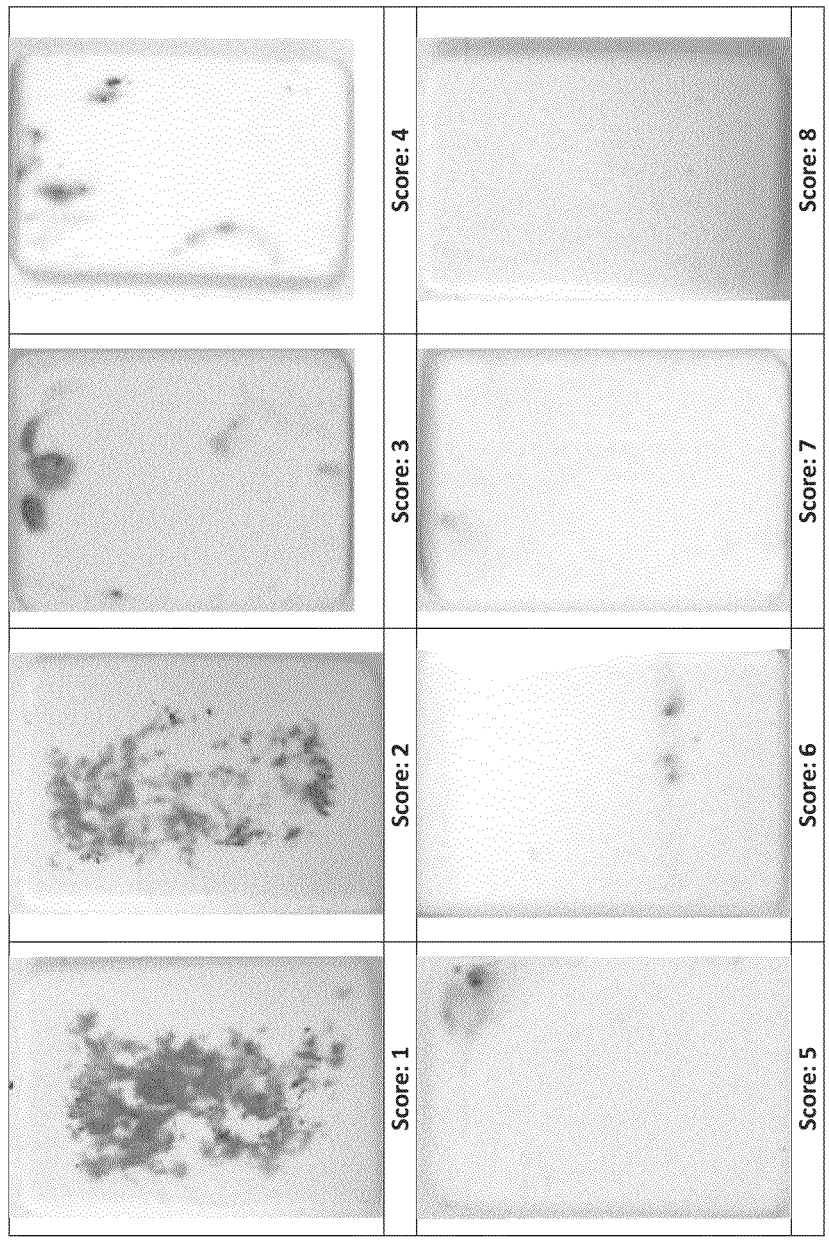
FIG. 1 is a discoloration score table showing pictures of 8 different bar soap samples containing ZPT with discoloration scores ranging from 1 (most discolored) to 8 (least discolored), which can be used for panel evaluation of ZPT discoloration in exemplary and comparative bar soap compositions.

"Bar soaps" as used herein refers to solid or semi-solid articles for washing, bathing, and cleaning that contain either soap surfactants, synthetic surfactants, or mixtures thereof (i.e., semi-synthetics) as described hereinafter. A bar soap as used herein is not limited to a bar shape but can have any regular or irregular shape, including but not limited to: cubic, rectangular, spherical, oval, cylindrical, pyramidal and the like. The bar soaps of the present invention are preferably, but not necessarily, characterized by a volume ranging from 1 $cm^3$ to 1,000 $cm^3$, more preferably from 10 $cm^3$ to 500 $cm^3$, and most preferably from 50 $cm^3$ to 200 $cm^3$, and a weight ranging from 0.5 g to 5 Kg, more preferably from 1 g to 1 Kg, and most preferably from 10 g to 500 g.

Except as otherwise noted, the articles "a", "an", and "the" mean "one or more." The term "substantially free of" refers to the presence of a compound or material at an amount of less than 0.1% by total weight of the composition in issue. The term "comprising" means that other steps and other ingredients which do not affect the end result can be added, and this term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein. Particularly, the compositions of the present invention contain ZPT, a metal-phosphonate complex, and at least one soap surfactant as the essential ingredients, and they may contain one or more additional or optional ingredients as described hereinafter.

All percentages, parts and ratios are based upon the total weight of the personal cleansing compositions of the present invention, unless otherwise specified. All such weights as they pertain to listed ingredients are based on the active level and, therefore do not include carriers or by-products that may be included in commercially available materials.

All ratios are weight ratios unless specifically stated otherwise. All temperatures are in Celsius degrees, unless specifically stated otherwise. All dimensions and values disclosed herein (e.g., quantities, percentages, portions, and proportions) are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm."

Herein, the term "effective" means an amount of a subject active high enough to provide a significantly positive modification of the condition to be treated. An effective amount of the subject active will vary with the particular condition being treated, the severity of the condition, the duration of the treatment, the nature of concurrent treatment, and like factors.

The present invention relates to a personal cleansing composition, preferably a bar soap composition, that comprises the combination of ZPT and a metal-phosphonate complex that contains one or more phosphonate chelants coordinately bonded to one or more metal ions. In an embodiment, the metal in the metal-phosphonate complex is selected from the group consisting of iron, copper and zinc. However, it will be understood by one skilled in the art that other metals can be selected according to the Irving Williams Series.

Such a personal cleansing composition exhibits substantially extended shelf life by stabilizing ZPT against potential environmental assaults and thereby reducing loss of effective amount of ZPT over time, in comparison with compositions containing ZPT alone or ZPT with uncomplexed phosphonate chelants. Without wishing to be bound by theory, according to Irving Williams Series, a more stable complex can be formed between phosphonate and metal ions having smaller ionic radius. For example, $Fe^{3+}$ has a radius of 0.64 A, which is smaller than $Cu^{2+}$ which has a radius of 0.73 A, and which is in turn smaller than that of $Zn^{2+}$ 0.74 A. Thus, this might help to explain why you have pyrithione discoloration in ZPT-containing bar soaps in the presence of other transition metal sources (e.g., copper and iron).

Further, such a personal cleansing composition exhibits enhanced color stability or discoloration resistance in the presence of high concentration of ferric or cupric ions, in comparison with compositions containing ZPT alone or ZPT with uncomplexed phosphonate chelants. Without being bound by any particular theory, it is believed that the presence of the Zn-phosphonate complex in a bar soap composition is particularly effective in inhibiting or retarding transchelation between dissolved pyrithione (PT) ions and ferric or cupric ions and formation of colored precipitates, thereby eliminating or significantly reducing discoloration.

Although bar soap is the preferred product form for carrying the combination of ZPT and metal-phosphonate complex, the scope of the present invention is not thus limited. Instead, the present invention may also encompass other product forms of rinse-off personal cleansing compositions, which include but are not limited to: body washes, shower gels, liquid hand soaps, shampoos, conditioners, facial cleansers, and the like.

Zinc Pyrithione (ZPT)

Zinc pyrithione (ZPT) is incorporated in the personal cleansing compositions of the present invention in the form of a combination, a mixture, a dispersion, a suspension, or an emulsion. Preferably, but not necessarily, ZPT is present in a spherical or platelet form, while the ZPT particles have an average size of up to about 20 microns, more preferably up to about 10 microns, even more preferably up to about 5 microns, and most preferably up to about 2.5 microns. Alternatively, ZPT is present in a particulate form that is non-platelet and non-spherical, having a configuration selected from the group consisting of rods, needles, cylinders, cones, ellipsoids, prisms, parallelepipeds, pyramids, tetrahedrons, hexahedrons, octahedrons, dodecahedrons, icosahedrons, and combinations thereof, as described by U.S. Pat. No. 6,242,007.

In a preferred embodiment of the present invention, the ZPT included in the bar soap composition is a dry powder ZPT in platelet particle form ("platelet ZPT"). Such platelet ZPT can have a median particle diameter of, for example, from about 0.05 to about 10 microns, alternatively from about 0.1 to about 8 microns, and alternatively from about 0.2 to about 5 microns, and alternatively about 3 microns. The platelet ZPT can also have a thickness of, for example, from about 0.1 to about 15 microns, alternatively from about 0.5 to about 1 micron, alternatively from about 0.6 to about 0.8 microns, and alternatively from about 0.6 to about 0.7 microns, as described in U.S. Patent Publication 2012/0219610.

ZPT as used in the present invention may be made by reacting 1-hydroxy-2-pyridinethione (i.e., pyrithione acid) or a soluble salt thereof with a zinc salt (e.g., $ZnSO_4$) to form a ZPT precipitate, as illustrated by the disclosures of U.S. Pat. No. 2,809,971, or processed into platelet ZPT using, for example, sonic energy as illustrated by U.S. Pat. No. 6,682,724, or by any other methods currently known in the art. While higher concentrations of ZPT have been observed to control the growth of a wider range of micro-organisms, the useful amount of ZPT that can be added to a commercial product is limited by efficacy, economic considerations, regulatory restrictions, and environmental concerns. In personal cleansing compositions, such as soaps, the amount of ZPT that may be added is further limited by toxicological concerns. Preferably, but not necessarily, the bar soap compositions of the present invention contains ZPT in the amount ranging from about 0.01% to about 5% by total weight of such compositions. More preferably, such compositions contains from about 0.1% to about 2.0% ZPT by total weight.

Metal-Phosphonate Complex

The personal cleansing compositions of the present invention further comprise a metal-phosphonate complex, which comprises one or more phosphonate chelants that are coordinately bonded to one or more metal ions. In an embodiment, the metal is selected from the group consisting of iron, copper and zinc. However, it will be understood by one skilled in the art that other metals can be selected according to the Irving Williams Series, which refers to the relative stability of complexes formed by a metal ion. Without wishing to be bound by theory, according to Irving Williams Series, a more stable complex can be formed between pyrithione and metal ions having smaller ionic radius. For example, $Fe^{3+}$ has a radius of 0.64 A, which is smaller than $Cu^{2+}$ which has a radius of 0.73 A, and which is in turn smaller than that of $Zn^{2+}$ 0.74 A. Thus, this might help to explain why you have pyrithione discoloration in ZPT-containing bar soaps in the presence of other transition metal sources (e.g., copper and iron).

In a preferred embodiment, the metal is zinc. Such zinc-phosphonate complex has a surprising and unexpected effect on stabilizing the ZPT against potential environmental attacks and improving the discoloration resistance of the ZPT-containing personal cleansing compositions, which is demonstrated by a significant increase in its resistance to laboratory-induced discoloration in comparison with control samples containing ZPT only or with uncomplexed phosphonate chelant.

In a particularly preferred embodiment of the present invention, the phosphonate chelant comprises one or more functional groups of the formula:

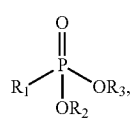

(I)

wherein $R_1$ is a linear, branched or cyclic, saturated or unsaturated, substituted or unsubstituted $C_1$-$C_{20}$ hydrocarbon group, and wherein $R_2$ and $R_3$ are independently selected from the group consisting of hydrogen and $R_1$. Preferably, both $R_2$ and $R_3$ are hydrogen.

Exemplary phosphonate chelants that are suitable for practice of the present invention include, but are not limited to: 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, and nitrilotrimethylene phosphonic acid (NTP).

A representative species of phosphonate chelant that is particularly useful for the practice of the present invention is HEDP, which has the chemical structure of:

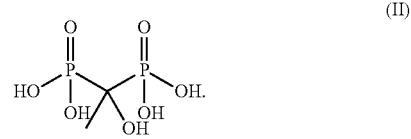

(II)

As a chelant, HEDP is capable of forming coordination complexes with transition metal ions in solution. Specifically, one or more HEDP can be bonded to one or more zinc ions to form a Zn-HEDP complex, which is a particularly preferred Zn-phosphonate compound for the present invention. It is important to note that zinc ions may be able to form various complexes with HEDP, with one or more HEDP attached to one or more zinc ions. In solution, zinc ions and HEDP may undergo speciation to form a mixture of different complex species, and the relative concentration of such complex species can vary depending on the chemical environment they are in, such as pH and the presence of other metal ions or chelant species. For ease of reference, all such complex species are herein referred to as the "Zn-HEDP complex," regardless of the actual number of HEDP or zinc ions included, and they are all included within the scope of the present invention.

The amount of zinc-phosphonate complex present in the bar soap compositions of the present invention may range from about 0.01% to about 10% by total weight of such compositions. More preferably, such compositions contains from about 0.05% to about 7% zinc-phosphonate complex, still more preferably from about 0.1% to about 7% or from about 0.5% to about 5%, and most preferably from 1% to 3% by total weight.

The zinc-phosphonate complex as used in the present invention can be pre-formed by reacting the phosphonate chelant with zinc oxide or a soluble zinc salt, such as $ZnSO_4$, $ZnCl_2$, or a mixture thereof. The reactant solution can then be added into the personal cleansing compositions.

Alternatively, the zinc-phosphonate complex can be formed in situ by directly adding the precursors, i.e., the phosphonate chelant and zinc oxide or the soluble zinc salt, into the personal cleansing compositions, which will directly complex with each other in the compositions. The phosphonate compound and zinc oxide or zinc salt can be added either in dry power form or pre-dissolved/dispersed in a solution.

The molar ratio of ZPT to Zn-phosphonate complex in the personal cleansing compositions of the present invention is preferably ranging from 5:1 to 1:10, more preferably from 2:1 to 1:5, still more preferably from 1:1 to 1:3, and most preferably about 1:1.5 to 1:2.

pH and pH Adjusting Agents

When the personal cleansing compositions of the present invention are in form of bar soaps, they are preferably characterized by a pH value ranging from 9.9 to 10.7 when dispersed in a 1 wt % aqueous solution. More preferably, the bar soap compositions have a pH range of 10.1 to 10.6, and most preferably from 10.2 to 10.5. This pH range is particularly beneficial for maintaining the dissolution equilibrium of ZPT and the Zn-phosphonate complex in the soap compositions, and can thereby extend or maximize the shelf life of the bar soaps.

The pH of the personal cleansing compositions of the present invention can be readily adjusted or modulated by various mechanisms. For example, the pH modulation can be achieved by adjusting the amounts of raw materials used for soap-making, i.e., fats, oils, and base materials such as sodium or potassium hydroxide, so as to reach a final personal cleansing composition with the desired pH value. For another example, the pH modulation can be achieved using a pH buffering agent, such as potassium carbonate or zinc carbonate. Further, the pH modulation can also be achieved through employment of an acidic pH adjusting agent.

In a preferred, but not necessary, embodiment of the present invention, the pH modulation is achieved by using an acid. Not all acids are suitable for practice of the present invention, and it has been observed that certain acids will aggravate the ZPT discoloration, while other acids help to reduce or alleviate it.

Particularly, it has been discovered that acids having an acid dissociation constant (pKa) of no more than 10 measured at a temperature of 25° C. and an ferric ion-complex stability constant (log K1) of no more than 8 measured at a temperature of 25° C. and an ion strength of 0.1M are particularly effective in reducing or alleviating the ZPT discoloration problem. The term "ferric ion-complex stability constant" as used herein refers to the stability constant of a complex formed between the acid of interest and ferric ions. Preferably, the acids are characterized by a pKa of no more than 8 and a log K1 of no more than 6 measured under the same conditions as described hereinabove. More preferably, the acids are characterized by a pKa of no more than 6 and a log K1 of no more than 4, as measured under the same conditions as described hereinabove.

Most preferably, acids used for practice of the present invention are selected from the group consisting of sulfuric acid, nitric acid, phosphoric acid, lactic acid, formic acid, acrylic acid, pyruvic acid, malonic acid, glyceric acid, glycine, L-alanine, β-alanine, methylglycine, maleic acid, dihydroxytartaric acid, creatinine, asparagine, N-glycylglycine, butanoic acid, betaine, valine, N-propylglycine, 5-aminopentanoic acid, trimethylacetic acid, pentanoic acid, benzoic acid, $C_6$-$C_{22}$ fatty acids, and combinations thereof. Fatty acids are particularly preferred acidic pH adjusting agents for the practice of the present invention.

Any fatty acids with total carbon numbers ranging from $C_6$ to $C_{22}$ can be used for the practice of the present invention. Exemplary fatty acids include, but are not limited to: caproic acid, caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and the like. Particularly useful fatty acids for the practice of the present invention are saturated or unsaturated fatty acids with total carbon numbers ranging from $C_{12}$ to $C_{22}$, such as, for example, lauric acid, myristic acid, palmitic acid, stearic acid, palmitoleic acid, oleic acid, and behenic acid.

In contrast, certain acids, such as hydrochloric acid, citric acid, aspartic acid, picolinic acid, 4-pyridinecarboxylic acid, 3-pyridinecarboxylic acid, tartaric acid, oxalic acid and glutamic acid, have been found to further aggravate the ZPT discoloration problem. It is therefore desirable, although not necessarily, to formulate the personal cleansing compositions of the present invention with as little of these types of acids as possible. Preferably, the personal cleansing compositions of the present invention are substantially free of hydrochloric acid, citric acid, aspartic acid, picolinic acid, 4-pyridinecarboxylic acid, 3-pyridinecarboxylic acid, tartaric acid, oxalic acid, glutamic acid, or any combination thereof.

Reducing Agents

The personal cleansing compositions of the present invention may optionally comprise one or more reducing agents, which are preferably, but not necessarily, selected from sterically hindered phenols. Such reducing agents can further improve the discoloration resistance of the soap compositions as well as extending the shelf life thereof.

Sterically hindered phenolic reducing agents suitable for the use of the present invention are characterized by a molecular weight above 500 Da. Preferred examples include 2,4-dimethyl-6-octyl-phenol; 2,6-di-t-butyl-4-methyl phenol (i.e., butylated hydroxy toluene); 2,6-di-t-butyl-4-ethyl phenol; 2,6-di-t-butyl-4-n-butyl phenol; 2,2'-methylenebis(4-methyl-6-t-butyl phenol); 2,2'-methylenebis(4-ethyl-6-t-butyl phenol); 2,4-dimethyl-6-t-butyl phenol; 4-hydroxymethyl-2,6-di-t-butyl phenol; n-octadecyl-beta(3,5-di-t-butyl-4-hydroxyphenyl)propionate; 2,6-dioctadecyl-4-methyl phenol; 2,4,6-trimethyl phenol; 2,4,6-triisopropyl phenol; 2,4,6-tri-t-butyl phenol; 2-t-butyl-4,6-dimethyl phenol; 2,6-methyl-4-didodecyl phenol; tris(3,5-di-t-butyl-4-hydroxy isocyanurate, and tris(2-methyl-4-hydroxy-5-t-butylphenyl)butane.

More preferred are pentaerythrityl tetra-di-t-butyl hydroxyhydrocinnamate (Tinoguard® TT, BASF); octadecyl-3,5-di-t-butyl-4-hydroxy-hydrocinnamate (NAUGARD 76, Uniroyal Chemical; IRGANOX 1076, Ciba-Geigy); tetrakis+methylene(3,5-di-t-butyl-4-hydroxy-hydrocinnamate) }methane (NAUGARD 10, Uniroyal Chemical; IRGANOX 1010, Ciba-Geigy); 2,2'-oxamido bis+ethyl-3-(3,5-di-t-butyl-4-hydroxyphenyl)}propionate (NAUGARD XL-1, Uniroyal Chemical); 1,2-bis(3,5-di-t-butyl-4-hydroxyhydrocinnamoyl)hydrazine (IRGANOX MD 1024, Ciba-Geigy); 1,3,5-tris(3,5-di-t-butyl-4-hydroxybenzyl)-s-triazine-2,4,6 (1H,3H,5H)trione (IRGANOX 3114, Ciba-Geigy); 1,3,5-tris (4-t-butyl-3-hydroxy-2,6-dimethylbenzyl)-s-triazine-2,4,6-(1H,3H,5H)trione (CYANOX 1790, American Cyanamid Co.); 1,3,5-trimethyl-2,4,6-tris(3,5-di-t-butyl-4-hydroxybenzyl)benzene (ETHANOX 330, Ethyl Corp.); 3,5-di-t-butyl-4-hydroxyhydrocinnamic acid triester with 1,3,5-tris(2-hydroxyethyl)-5-triazine-2,4,6(1H,3H,5H)-trione, and bis(3,3-bis(4-hydroxy-3-t-butylphenyl)butanoic acid)glycolester.

Most preferred reducing agents for the practice of the present invention are pentaerythrityl tetra-di-t-butyl hydroxyhydrocinnamate, which is commercially available under the trade name of Tinogard® TT from BASF (Monheim, Germany).

The amount of reducing agent present in the personal cleansing compositions of the present invention may range from about 0.001% to about 5% by total weight of such compositions. More preferably, such compositions contains from about 0.01% to about 1% of the reducing agent, and most preferably from about 0.02% to about 0.5%, by total weight of such compositions.

Soap Surfactants

The bar soap of the present invention will typically comprise a soap surfactant, or in short "soap", in an amount ranging from about 40%, 45%, 50% to about 65%, 75%, 84%. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof are suitable for purposes of the present invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

It can be preferred to use soaps having the fatty acid distribution of tallow and vegetable oil (i.e., "fatty acid soaps"). More preferably, the vegetable oil is selected from the group consisting of peanut oil, rapeseed oil, corn oil, olive oil, palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are $C_{16}$ and higher. A preferred soap is sodium soap having a mixture of about 50% tallow, 30% palm oil stearine, and 20% palm kernel oil or coconut oil.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

Synthetic Surfactants

Synthetic surfactants can be utilized in the present bar soap compositions, either in combination with or in place of the soap surfactants described hereinabove, to further improve the lathering properties of the bar soap during use. When a majority of the surfactants in the bar soap compositions of the present invention are synthetic surfactants rather than soap surfactants, the pH value of the bar soap compositions can be readily broaden to the relatively lower pH range of 7-9. In certain embodiments, the pH value of such bar soap compositions may approach the neutral pH range of 6-8, which is particularly beneficial because the resulting bar soaps are more gentle and less irritating to the skin.

The synthetic surfactants useful in this invention include anionic, amphoteric, nonionic, zwitterionic, and cationic surfactants. Synthetic surfactants are typically incorporated in the present compositions at a level of from about 0.1% to about 20%, preferably from about 0.5% to about 10%, and more preferably from about 0.75% to about 5%, by weight of the composition.

Examples of anionic surfactants include but are not limited to alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are $C_8$-$C_{22}$, preferably $C_{10}$-$C_{18}$ and, more preferably, $C_{12}$-$C_{14}$ alkyls.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3-dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378. Other amphoterics such as betaines are also useful in the present composition. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyet-hyl betaine, etc. The sulfobetaines may be represented by coco dimethyl sulfopropyl betaine, stearyl dimethyl sulfopropyl betaine, amido betaines, amidosulfobetaines, and the like.

Examples of suitable cationic surfactants include stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow(Hydrogenated) dimethyl ammonium chloride; dilauryldimethyl ammonium chloride; and stearalkonium chloride; and other cationic surfactants known in the art.

Nonionic surfactants useful in this invention can be broadly defined as compounds produced by the condensation of alkylene oxide groups (hydrophilic in nature) with an organic hydrophobic compound, which may be aliphatic or alkyl aromatic in nature.

A preferred synthetic surfactant for use in the present compositions is sodium laureth-3 sulfate. Sodium laureth sulfate tends to provide excellent lathering properties, especially when combined with sodium tripolyphosphate as the inorganic salt in the present compositions.

Other Ingredients

The personal cleansing compositions of the present invention can additionally comprise inorganic salts (especially inorganic zinc salts, such as zinc carbonate, zinc sulfate, zinc nitrate, zinc fluoride, zinc chloride, zinc borate, and the like as well as zinc oxide). A particularly preferred inorganic salt is zinc carbonate. In a particularly preferred embodiment of the present invention, the personal cleansing compositions contain zinc carbonate at an amount ranging from about 0.01% to about 5%, more preferably from about 0.1% to about 3%, and most preferably from about 1% to about 2% by total weight of the composition. Zinc carbonate provided at such an amount is particularly effective in reducing or removing malodor.

The personal cleansing compositions of the present invention may further comprise one or more optional ingredients selected from the group consisting of: structurants, such as raw starch, pregelatinized starch, carboxymethyl cellulose, polyacrylate polymer, Carbopol, carregeenan, xanthan gum, polyethylene glycol, polyethylene oxide, and the like; free fatty acids, such as those derived from tallow, coconut, palm and palm kernel; humectants; cationic polymers, such as cationic polysaccharides, cationic polyalkylene imines, cationic hydroxyethyl cellulose, and the like; brighteners; fillers, such as silica, talc, and the like; perfumes; sequestering agents; coloring agents; opacifiers and pearlizers, such as titanium dioxide.

All of these are useful in enhancing the appearance, smell or other cosmetic/sensory properties of the product. As bar soaps, the appearance of the personal cleansing compositions of the present invention can be transparent, translucent, or opaque, and the color thereof can be white, off-white, cream, yellow, pink, red, green, purple, blue and black. In one embodiment, the bar soap composition is opaque with a white or off-white color.

Preparation Methods

Bar soap compositions of the present invention can be made via a number of different processes known in the art. Preferably, the present compositions are made via a milling process, resulting in milled bar soap compositions. A typical milling process of manufacturing a bar soap composition includes: (a) a step in which the soap is made through either a continuous process (ConSap or continuous saponification process) or a batch-making process (i.e. neutralization process for hydrolysis fatty acid noodle or kettle process), (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition. The present bar soap can be made using any of the above mentioned manufacturing processes, and the ZPT, the metal-phosphonate complex (or the precursors for in situ forming such complex), and pH adjusting agent, and the reducing agent can be added during the mixing steps of preparing the bar soaps.

Other product forms of the present invention, such as body washes, shower gels, liquid hand soaps, shampoos, facial cleansers, and the like, can be readily formed by the conventional mixing or homogenization process.

Clinical Benefits

The personal cleansing compositions of the present invention have demonstrated various clinical benefits, which include but are not limited to: anti-microbial, de-germing, anti-dandruff, efficacy against atopic dermatitis, odor control, and the like.

Discoloration Test

As used herein, "discoloration" means the color change brought by formation of colored precipitates from a reaction between ZPT and unwanted metal ions, such as ferric ions and/or cupric ions. The discoloration can be in a color of grayish blue, blue, black, purple, green, and the like, which is different from the original color of a composition comprising ZPT. By "original color", it means the color of the composition before ZPT in the bar soap has an opportunity to react with ferric and/or cupric ions. For ease of measurement and comparison, discoloration in bar soaps herein is artificially induced by adding solutions containing ferric and/or cupric ions, and the color difference in the bar soaps before and after the artificial introduction of ferric and/or cupric ions can be readily measured either by employing an expert panel trained for conducting discoloration evaluation or quantitatively by using a colormeter or other well known equipment.

For example, a Wet Iron Plate method can be used to artificially induce ZPT discoloration in bar soaps. Specifically, cast iron plates are chosen as the ferric source to react with the pyrithione ions to induce discoloration. Before testing, the cast iron plates are polished to make sure that there is no rust on the surface. Then, the cast iron plates and the bar soaps to be tested are washed under running tap water for 5 minutes. Then, the wet bar soaps are carefully placed on the wet cast iron plates to ensure sufficient contact between the bar soaps and the surfaces of the cast iron plates. The bar soaps are kept on the cast iron plates for 2 hours before they are removed. Resulting discoloration on the bar soaps is then evaluated by a panel of 6 panelists who grade the discoloration according to the discoloration score table shown in FIG. 1. Specifically, FIG. 1 includes pictures of 8 different bar soap samples containing ZPT with discoloration scores ranging from 1 (most discolored) to 8 (least discolored), which can be used for panel evaluation of discoloration of exemplary and comparative bar soap compositions.

Alternatively, a Ferric Ion Discoloration Threshold method can be used to evaluate the resistance of bar soap compositions against ferric ion-induced discoloration. The "threshold" means the minimum level of undesirable metal ions for causing measurable color change in ZPT bar soap, which can be determined by a tangential extrapolation process as described hereinafter.

Specifically, when a bar soap composition is ready to be tested for discoloration threshold, it is processed into multiple sample bar soaps. A circular surface area with a diameter of 23.50 mm is marked on the surface of each sample bar soap. Such a circular surface perfectly matches the diameter of a probe in a Gretag-Macbeth™ Color-Eye 3100 colormeter, which is employed in the present invention to measure the color LAB values of the sample bar soaps before any discoloration was induced by introduction of ferric ions ("Standard Color").

Subsequently, a series of freshly prepared $FeCl_3$ solutions containing 0.0029 wt %, 0.0058 wt %, 0.0087 wt %, 0.0116 wt %, 0.0174 wt %, 0.0232 wt %, and 0.0290 wt % of $FeCl_3$ are separately titrated onto the marked circular surface areas of seven (7) sample bar soaps made from the same bar soap composition to be tested, so as to intentionally induce discoloration therein. The volume of each $FeCl_3$ solution on each circular surface area is well controlled to be 60 μl. Therefore, the levels of $Fe^{3+}$ ions titrated onto the sample bar soap surfaces are 8.1 ppm, 16.1 ppm, 21.2 ppm, 28.3 ppm, 42.4 ppm, 56.5 ppm, and 70.7 ppm, respectively.

After being placed under room temperature for 2 hours, various degrees of discoloration will develop on the top layer of the sample bar soaps within the marked circular surface area where the $FeCl_3$ solutions are titrated.

The marked circular surface area is then analyzed by the Gretag-Macbeth™ Color-Eye 3100 colormeter to determine the LAB color values of the discoloration induced by addition of the $FeCl_3$ solution ("Sample Color"). The colors are hereby quantified by the well-known LAB values. Specifically, the L value represents the lightness or brightness of the color measured, i.e., the higher the L value, the lighter or brighter the color. The A value represents the redness/greenness of the color measured, with positive A values stand for red colors and negative A values stand for green colors. The B value represents the yellowness/blueness of the color measured, with positive B values stand for yellow colors and negative B values stand for blue colors. When comparing the difference between a Sample Color and a Standard color, a positive Delta L ($\Delta L$), which is calculated as $=L_{Sample}-L_{Standard}$, indicates that the Sample Color is lighter than the Standard Color, and a negative $\Delta L$ indicates that the Sample Color is darker than the Standard Color. A positive Delta A ($\Delta A$), which is calculated as $=A_{Sample}-A_{Standard}$, indicates that the Sample Color is redder, and a negative $\Delta A$ indicates that the Sample Color is green. A positive Delta B ($\Delta B$), which is calculated as $=B_{Sample}-B_{Standard}$, indicates that the Sample Color is yellower, and a negative $\Delta B$ indicates that the Sample Color is bluer. The more negative $\Delta B$ is, the more blue the Sample Color is in comparison with the Standard Color.

By plotting the measured $\Delta B$ values (y axis) against the titrated ferric levels (x axis) of the tested bar soap composition on a graph, a discoloration curve for the tested bar soap composition can be obtained. The minimum level of ferric ions needed for causing measurable blue color change in such tested bar soap composition can then be determined by extrapolation, i.e., by drawing a tangential line along the steepest portion of the discoloration curve plotted for the tested bar soap composition and extrapolating the tangential line to intersect with the x axis of the graph. The x value (i.e., the ferric level) that corresponds to the intersection point is then identified as the ferric ion discoloration threshold.

Figure 2:
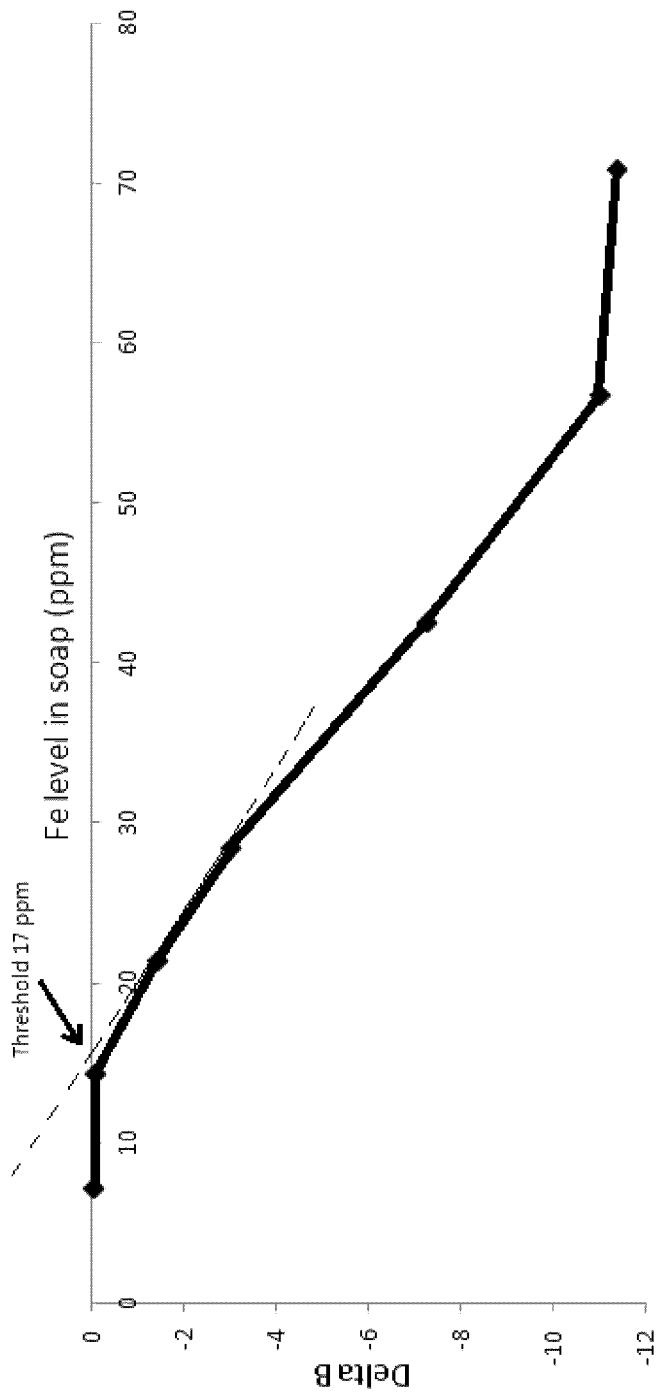
FIG. 2 is a discoloration curve of a ZPT-containing bar soap composition formed by plotting the Delta B (ΔB) values (i.e., blue discoloration) exhibited by such bar soap composition against various concentrations of $FeCl_3$ solutions used for titrating such bar soap composition and thereby artificially inducing ZPT discoloration therein.
Figure 3:
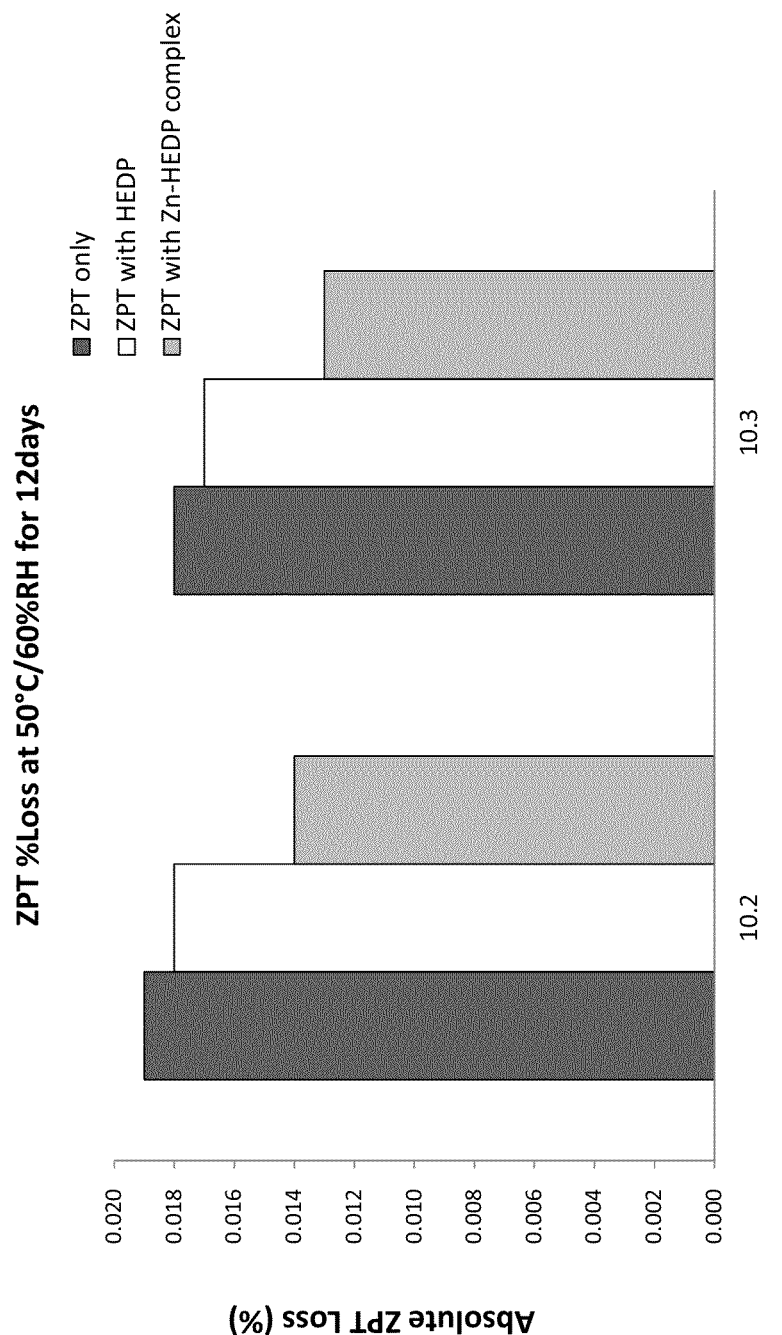
FIG. 3 is a graph showing the percentage loss of ZPT in two (2) exemplary bar soap compositions of the present invention and four (4) comparative bar soap compositions when placed at 50° C. and 60% relative humidity (RH) for 12 days. The exemplary and comparative bar soap compositions were compositionally similar except for the presence or absence of Zn-HEDP complex.

For purpose of illustration, FIG. 2 shows a discoloration curve of a ZPT-containing bar soap composition, which is formed by plotting the Delta B ($\Delta B$) values (i.e., blue discoloration) exhibited by such a bar soap composition (i.e., the y axis) against various $Fe^{3+}$ levels used (i.e., the x axis) for titrating such bar soap composition to artificially induce ZPT discoloration therein. The dotted line is a tangential line drawn along the steepest portion of the discoloration curve, which intersects with the x axis. The intersection point, as highlighted by the arrowhead, corresponds to a $Fe^{3+}$ level of 17 ppm, which is defined as the ferric ion discoloration threshold (i.e., the minimum amount of ferric ions required for artificially inducing discoloration) for the bar soap composition of interest. The higher this threshold, the more resistant the composition is against discoloration.

ZPT Stability

As mentioned hereinabove, zinc pyrithione (ZPT) may undergo transformation upon exposure to oxidizing species, thereby losing its anti-microbial effect over time in environments susceptible to oxidation. Such vulnerability of ZPT to environmental assaults is well known in the art, and various solutions have been proposed to stabilize ZPT with limited success.

It is a surprising and unexpected discovery of the present invention that the above-described Zn-phosphonate complex is effective in stabilizing ZPT in bar soap compositions and reducing ZPT loss even in harsh chemical environments.

The chemical stability of ZPT is evaluated by an aging test described as follows, so as to determine the percentage loss of ZPT after such aging test. First, a bar soap containing ZPT is obtained, preferably immediately after it is manufactured. The starting content of ZPT in such bar soap (in percentage) is measured by method described hereinafter using a portion of the bar soap, or a companion bar made from the same batch of soap noodle. The bar soap is weighed (+/−0.01 g), and its starting weight is recorded. Second, the bar soap is subjected to an aging process, during which the bar soap is placed inside a sealed water impermeable bag, which is preferably made of polyethylene (PE). The bag containing the bar soap is then left either at room temperature (i.e., about 25° C.), or in a convection oven at an elevated temperature (e.g., 50° C.), for an extended period (e.g., 10 days, 12 days, 14 days, or up to 36 months in certain cases). After the aging, if placed in a convection oven at the elevated temperature, the bar soap is taken out of the convection oven and allowed to return to room temperature (i.e., 25° C.). The bar soap is weighed again, and its final weight is recorded. The final content of zinc pyrithione in the bar soap (in percentage) is measured by the same method as described hereinafter.

Chemical stability of the ZPT is calculated by the following equation to obtain the percentage loss of ZPT:

$$\% \text{ Loss of } ZPT = \left[1 - \frac{\text{Final Bar Weight} \times \text{Final } ZPT \text{ Content }(\%)}{\text{Starting Bar Weight} \times \text{Starting } ZPT \text{ Content }(\%)}\right] \times 100\%,$$

The content of ZPT in bar soap compositions is measured herein by an iodine-based titration method, which is described in greater detail in the following sections. The mercapto group in ZPT can be titrated by iodine, which oxidizes it to the disulfide-2,2' dithiobispyridine-l-oxide. If ZPT has already been oxidized or undergone transformation otherwise so that it no longer possesses the mercapto group, it will not be detectable by the iodine-based titration method described hereinafter.

First, a standardized 0.04N iodine solution is prepared. Specifically, anhydrous sodium thiosulphate (with a minimum purity of 99%) is oven-dried for 2 hours at 105° C. and then stored in a dessicator. 0.05 grams (+/−0.0001 g) of the anhydrous sodium thiosulfate is weighed and placed into the 100 ml polypropylene beaker of an autotitrator, and 50 ml of deionized water is added to form a standard solution. The autotitrator used herein is preferably a Mettler DL25 or Mettler DM140-SC titrator with platinum ring electrode, which is commercially available from Mettler Toledo International, Inc. (Switzerland), or an equivalent thereof. The autotitrator is set up to titrate the standard sodium thiosulfate solution with the iodine solution that is being standardized. Bubbles are eliminated from the burette of the autotitrator, and titration is commenced. Such procedure is repeated twice more, and the results are averaged to obtain a standardized 0.04N iodine solution. The % relative standard deviation (RSD) should be less than 1% of the average.

Next, standardized 0.01N and 0.006N iodine solutions are prepared. Specifically, standardized 0.1N iodine solution is prepared using 0.10 g (+/−0.0001 g) sodium thiosulphate dissolved in 100 mL deionized water, using 10.0 mL pipetted into the 100 mL autotitrator breaker with 50 mL additional deionized water followed by the titration procedure. Standardized 0.006N iodine solution is prepared using 3.0 mL of a 0.01M sodium thiosulphate solution and 40 mL of a solvent (containing 13% v/v hydrochloric acid in 6% v/v butanol), followed by addition of 40 mL of 1:1 hexane/isopropanol. The autotitration procedure is subsequently carried out. The iodine solutions are standardized daily.

The bar soap whose ZPT content is to be measured is then shredded using a grater and stirred to form a homogenous mixture. 4.00 grams of the shredded soap is weighed and put into a clean, dry beaker of an autotitrator. 75 ml of hot 6% v/v butanol (which was heated in a boiling-water bath) and 5 mL of concentrated HCl (provided at room temperature) are then added into the beaker. The mixture is agitated vigorously so as to fully dissolve all soluble components. The beaker is subsequently placed in the autotitrator, and bubbles are completely eliminated from the burette.

The titration is then initiated and analyzed while the mixture is still warm. The mixture is vigorously agitated during the titration procedure. For compositions with less than 0.2% of ZPT by weight, titration is carried out using the 0.006N iodine solution. For compositions with higher ZPT concentrations, the initial starting sample weight can be reduced. Titration can be done either manually or by using autotitration procedure by those with skill in the art.

The ZPT content in the bar soap is calculated as follows:

$$ZPT\ Content\ (\%) = \frac{Volume\ of\ Iodine\ Solution\ (ml) \times N \times 15.88\%}{Sample\ Weight\ (g)},$$

wherein N is the normality of the standardized iodine solution, and wherein 15.88% is a constant that is derived from:

$$15.88\% = \frac{Molecular\ Weight\ of\ ZPT \times 100\%}{Number\ of\ Pyrithione\ per\ Molecule \times 1000\ ml/Liter} = \frac{371.6 \times 100\%}{2 \times 1000\ ml/Liter},$$

The above-described procedure is repeated three times for each bar soap composition whose ZPT content is to be measured, and the results are averaged to obtain a final ZPT content in percentage (%) for the specific bar soap. All chemical reagents employed hereinabove are high-purity reagents obtained from VWR Scientific (Batavia, Ill., USA) or other scientific chemical suppliers.

pH Measurement

The pH value of a bar soap composition is measured in aqueous solution at about 25° C., and it can be measured using any commercially available pH meter calibrated with pH standard solutions, such as, for example, the SevenMulti™ pH meter available from Mettler Toledo International, Inc. (Switzerland). Specifically, a bar soap composition whose pH value is to be measured is first dissolved in distilled water at a concentration of 1 wt % and a temperature of 35° C. by agitation provided by a magnetic stir bar in a sealed container for one hour. The soap solution is then cooled to about 25° C. (+/−0.2° C.), and the pH is measured. The pH of the 1 wt % aqueous solution is then recorded as the pH of the bar soap composition.

Water Activity

Water Activity ("Aw") is a measurement of the energy status of the water in a system. It indicates how tightly water is bound, structurally or chemically, within a composition. Water activity ("Aw") is defined as the ratio of the water vapor pressure over a sample (P) to that over pure water ($P_0$):

$$A_W = \frac{P}{P_0}$$

Water activity of a bar soap composition can be measured electronically using a water activity meter with a sealed chamber and an electrical or optical measurement of the headspace. The meter is calibrated against a series of saturated salt solutions. A bar soap composition to be measured is placed in the chamber held at ambient temperature which is then allowed to equilibrate with the headspace in the chamber. At equilibrium, the relative humidity of the air in the chamber is the same as the water activity of the composition.

For purposes of the present invention, the water activity (Aw) of a bar soap composition can be measured using a Hygrolab 3 Water Activity Meter available from Rotronic, Inc. (Huntington, N.Y., USA). The following procedure is employed to determine the water activity (Aw) of a bar soap composition:

1. Check the chamber of the meter to make sure it is clean and dry before the test;
2. Cut a bar soap into pieces of about 0.2-0.4 cm thick with a stainless steel knife;
3. Put the soap pieces into a clean, dry plastic sample container with a depth of ½";
4. Press the soap pieces with a gloved finger lightly to make sure that the bottom of the container is covered by the soap pieces;
5. Put the sample container back into the chamber of the meter and cover it with the chamber top, which contains the electronic headspace measurement apparatus;
6. Wait for the headspace to reach equilibrium (approximately 1-2 hours); and
7. Record the temperature and the Aw value.

Preferably, but not necessarily, the bar soap compositions of the present invention are characterized by a water activity of less than 0.9, more preferably between about 0.4 and 0.9, still more preferably between 0.5 and 0.9, and most preferably between 0.6 and 0.9. The bar soap can be manufactured with a water activity of about 0.85, and during distribution, such bar soap can dehydrate to obtain a lower water activity of between 0.5 and 0.8, or between 0.55 and 0.75, or between 0.6 and 0.75.

Examples

I. Pre-Formation of Zinc-Phosphonate Complex

Zn-HEDP complex can be pre-formed by using the following raw materials:

TABLE I

| Zn/HEDP Precomplex formation: | | |
|---|---|---|
| Material Name | Nominal (%) | Target Weight (g) |
| HEDP—4Na | 10.00 | 80.00 |
| ZnSO4•7H2O* | 7.78 | 62.24 |
| Water (DI) | 82.22 | 657.76 |
| Total | 100.00 | 800.00 |

*Analytical grade available from Tianjin Jiaxin Chemicals Glass Instrument Trading Co., Ltd.

The following procedure is followed to pre-form the Zn-HEDP complex of the present invention:
Pre-weigh 300 grams of the deionized (DI) water, which is herein referred to as "DI water 1";
Pre-weigh 80 grams of HEDP-4Na;
Use a magnetic bar to stir up a vortex and then add the pre-weighed HEDP-4Na into the DI water 1 slowly;
Keep agitating until the solution turns clear without visible particles, which is herein referred to as the "HEDP solution";
Place the rest of DI water (357.76 grams) into a separate container, which is herein referred to as "DI water 2";
Pre-weigh 62.24 grams of ZnSO4.7H2O;
Use the magnetic bar to stir up a vortex and then add the pre-weighed ZnSO4.7H2O gradually into the DI water 2;
Keep agitating until the solution turns clear without visible particles, which is herein referred to as the "ZnSO$_4$ solution"; and
Add the ZnSO4 solution into the HEDP solution slowly. During this process, white gel like precipitation may appear in the solution, so it is important to keep agitating for about 30 minutes, thereby allowing such precipitation to dissolve and resulting in a final mixture that is transparent without noticeable precipitation or particulates therein.

Other zinc-phosphonate complexes can be readily formed by using other sodium phosphonate salts and following a similar procedure.

II. Phosphonate Solution

A HEDP solution can be prepared by using the following raw materials:

TABLE II

| Material Name | Nominal (%) | Target Weight (g) |
|---|---|---|
| HEDP—4Na | 10.00 | 80.00 |
| Water (DI) | 90.00 | 720.00 |
| Total | 100.00 | 800.00 |

Specifically, the HEDP solution is prepared by following the below procedures:
Pre-weigh 720.00 grams of DI water;
Pre-weigh 80 grams of HEDP-4Na;
Use a magnetic bar to stir up a vortex and then add the HEDP-4Na into the DI water slowly; and
Keep agitating until the solution turns clear without visible particles.

Such a HEDP solution can be used in comparative examples to compare the effect of Zn-HEDP complex with the uncomplexed HEDP chelant itself.

III. Comparative ZPT Stability Test

Six different bar soaps A-F are prepared containing ingredients as listed in Table III below. Specifically, Comparative Example A contains soap noodle with ZPT and a pH adjusting agent (i.e., 0.28% $H_2SO_4$). Comparative Example B contains soap noodle with ZPT, but without the pH adjusting agent. Comparative Example C contains soap noodle with ZPT, uncomplexed HEDP, and a pH adjusting agent (i.e., 0.40% $H_2SO_4$). Comparative Example C contains soap noodle with ZPT and the uncomplexed HEDP, but without the pH adjusting agent. Inventive Example E contains soap noodle with ZPT and a pH adjusting agent (i.e., 0.40% $H_2SO_4$) in combination of pre-formed Zn-HEDP complex. Inventive Example E contains soap noodle with ZPT in combination with the pre-formed Zn-HEDP complex, but without the pH adjusting agent.

TABLE III

| | Amount (w/w %) | | | | | |
|---|---|---|---|---|---|---|
| Raw Materials | A | B | C | D | E | F |
| Dry Soap Noodle** | 76.18 | 76.18 | 76.13 | 76.13 | 76.13 | 76.13 |
| TiO2 | 0.40 | 0.40 | 0.40 | 0.40 | 0.40 | 0.40 |
| H2SO4 | 0.28 | — | 0.40 | — | 0.40 | — |
| Starch | 17.00 | 17.00 | 17.00 | 17.00 | 17.00 | 17.00 |
| ZPT (48% active) | 0.42 | 0.42 | 0.42 | 0.42 | 0.42 | 0.42 |
| HEDP (10% solution) | — | — | 4.00 | 4.00 | — | — |
| Pre-formed Zn-HEDP (10% solution) | — | — | — | — | 4.00 | 4.00 |
| Perfume | 1.00 | 1.00 | 1.00 | 1.00 | 1.00 | 1.00 |
| Brightener 49 | 0.02 | 0.02 | 0.02 | 0.02 | 0.02 | 0.02 |
| Tinogard TT* | — | — | 0.05 | 0.05 | 0.05 | 0.05 |
| DI water | Q.S. | Q.S. | Q.S. | Q.S. | Q.S. | Q.S. |
| pH (1% solution) | 10.19 | 10.36 | 10.15 | 10.36 | 10.15 | 10.34 |

*Commercially available as Tinogard ® TT from BASF (Monheim, Germany)

**The soap noodle contained the following ingredients:

TABLE IV

| Ingredients | Wt % |
|---|---|
| Sodium palmate (from palm oil and palm oil sterine) | 49.683 |
| Sodium tallowate (from tallow) | 16.027 |
| Sodium palm kernelate (from palm kernel oil) | 14.424 |
| Unsaponifiable matter | 0.540 |
| Citric acid (anhydrous) | 0.100 |
| Sodium citrate | 0.152 |
| Pentasodium pentetate | 0.050 |
| Tetrasodum etidronate | 0.050 |
| Sodium chloride (low sodium) | 0.553 |
| Glycerine | 3.471 |
| Coconut acid | 0.950 |
| DI Water | Q.S. |

The initial weights and initial ZPT contents in the bar soaps of Comparative Examples A-D and Inventive Examples E and F are measured according to the ZPT stability test procedures described hereinabove. The bar soaps are then subjected to environment stresses in an incubator at 50° C. with 60% relative humidity (RH) for 12 days, after which the final weights and final ZPT contents were re-measured and used to calculate the percentage (%) loss of ZPT. The measurements results are as follows:

TABLE V

| Results | A | B | C | D | E | F |
|---|---|---|---|---|---|---|
| Initial ZPT Content (w/w %) | 0.207 | 0.202 | 0.194 | 0.204 | 0.196 | 0.203 |
| Final ZPT Content (w/w %) | 0.193 | 0.192 | 0.181 | 0.192 | 0.186 | 0.195 |
| Initial Bar Weight (g) | 44.83 | 43.62 | 44.23 | 44.15 | 43.69 | 44.39 |
| Final Bar Weight (g) | 43.62 | 42.13 | 43.04 | 43.16 | 42.77 | 43.38 |
| ZPT Loss (%) | 9.28 | 8.18 | 9.21 | 7.99 | 7.10 | 6.13 |

The ZPT losses (%) from the above Comparative and Inventive Examples are plotted in FIG. 2, which demonstrates that in the presence of uncomplexed HEDP, ZPT loss in bar soap compositions is comparable to that in compositions containing only ZPT. However, in the presence of Zn-HEDP complex, ZPT loss is significantly reduced.

IV. Comparative Discoloration Test

A. Uncomplexed HEDP vs. Zn-HEDP Complex

Six different bar soaps G-L are prepared containing ingredients as listed in Table VI below. Specifically, three Comparative Example G-I contain uncomplexed HEDP at concentrations of 0.5 wt %, 0.4 wt % and 0.3 wt %, respectively. Three Inventive Examples J-L contain pre-formed Zn-HEDP complex at concentrations of 0.89 wt %, 0.71 wt % and 0.53 wt %, respectively.

TABLE VI

| Ingredients (wt %) | G | H | I | J | K | L |
|---|---|---|---|---|---|---|
| Soap Noodle | 75.10 | 75.68 | 76.00 | 74.20 | 74.70 | 75.2 |
| ZPT | 0.20 | 0.20 | 0.20 | 0.20 | 0.20 | 0.20 |
| HEDP-4Na | 0.50 | 0.40 | 0.30 | 0 | 0 | 0 |
| Pre-formed Zn-HEDP complex (1:1 molar ratio) | 0 | 0 | 0 | 0.89 | 0.71 | 0.53 |
| TiO2 | 0.40 | 0.40 | 0.40 | 0.40 | 0.40 | 0.40 |
| Starch | 17.00 | 17.00 | 17.00 | 17.00 | 17.00 | 17.00 |
| Perfume | 1.00 | 1.00 | 1.00 | 1.00 | 1.00 | 1.00 |
| Brightener-49 | 0.02 | 0.02 | 0.02 | 0.02 | 0.02 | 0.02 |
| Water | Q.S. | Q.S. | Q.S. | Q.S. | Q.S. | Q.S. |

The ferric ion discoloration threshold of each of the above-described Comparative and Inventive Examples is then measured according to the Ferric Ion Discoloration Threshold test method discussed hereinabove, and the measurement results are listed in the following table alongside the respective molar levels of HEDP or Zn-HEDP in such examples (which are calculated based on the respective wt % of HEDP and Zn-HEDP):

TABLE VII

| | Level of HEDP or Zn-HEDP (mole/100 g soap) | Discoloration Threshold ($Fe^{3+}$ ppm) | pH (1%) |
|---|---|---|---|
| G | HEDP: $1.36 \times 10^{-3}$ | 70 | 10.41 |
| H | HEDP: $1.09 \times 10^{-3}$ | 110 | 10.48 |
| I | HEDP: $0.81 \times 10^{-3}$ | 60 | 10.38 |
| J | Zn-HEDP: $1.36 \times 10^{-3}$ | 200 | 10.46 |
| K | Zn-HEDP: $1.09 \times 10^{-3}$ | 110 | 10.27 |
| L | Zn-HEDP: $0.81 \times 10^{-3}$ | 110 | 10.27 |

It is clear from the above table that the discoloration threshold of bar soap compositions containing Zn-HEDP complex has shown significantly improvement in comparison with that in bar soap compositions containing uncomplexed HEDP at the same molar level.

B. The Effect of Reducing Agent on Discoloration

To assess the impact of a preferred reducing agent, pentaerythrityl tetra-di-t-butyl hydroxyhydrocinnamate, the following examples are prepared:

TABLE VIII

| Ingredients (wt %) | Example 1 | Example 2 | Example 3 |
|---|---|---|---|
| Soap Noodle* | 76.0~76.9 | 76.0~76.9 | 76.0~76.9 |
| ZPT | 0.20 | 0.20 | 0.20 |
| Citric Acid (for adjusting pH) | 0.1~1.0 | 0.1~1.0 | 0.1~1.0 |
| Pre-formed Zn-HEDP complex | 0.534 | 0.534 | 0.534 |
| Pentaerythrityl tetra-di-t-butyl hydroxyhydrocinnamate ("TT") | — | 0.025 | 0.05 |
| TiO2 | 0.40 | 0.40 | 0.40 |
| Starch | 17.00 | 17.00 | 17.00 |
| Perfume | 1.00 | 1.00 | 1.00 |
| Brightener-49 | 0.02 | 0.02 | 0.02 |
| Water | 3.846 | 3.821 | 3.796 |

*Same as described hereinabove in Table IV.

The wet iron plate method as described hereinabove is used to assess the degree of discoloration appeared in the above-identified soap compositions. The discoloration scores provided by the 6 panelists are averaged for each bar soap that is tested, so as to reach a final discoloration score. The discoloration scores of the above three bar soap compositions at different pH values are provided as follows:

TABLE IX

| pH (1%, 25° C.) | Discoloration Grading | | |
|---|---|---|---|
| | Example 1 | Example 2 | Example 3 |
| 10.00~10.10 | 1 (pH = 10.05) | 1 (pH = 10.01) | 1 (pH = 10.00) |
| 10.11~10.20 | 1 (pH = 10.18) | 1.4 (pH = 10.12) | 1.5 (pH = 10.17) |
| 10.21~10.25 | 1 (pH = 10.25) | 1.9 (pH = 10.24) | 1.9 (pH = 10.24) |
| 10.25~10.30 | 1 (pH = 10.29) | 2.4 (pH = 10.27) | 2.6 (pH = 10.29) |
| 10.30~10.40 | 2.4 (pH = 10.35) | 2.9 (pH = 10.34) | 3.4 (pH = 10.33) |
| | 3.2 (pH = 10.39) | 3.4 (pH = 10.39) | |
| 10.41~10.5 | 3.6 (pH = 10.44) | NA | 3.8 (pH = 10.45) |

The above discoloration scores shows that the presence of a reducing agent, i.e., pentaerythrityl tetra-di-t-butyl hydroxyhydrocinnamate, in the bar soap compositions of the present invention further reduces ZPT discoloration.

V. Exemplary Bar Soap Compositions

Following are a few exemplary bar soap compositions within the scope of the present invention:

TABLE X

| | Amount (w/w %) | | | |
|---|---|---|---|---|
| Raw Materials | I | II | III | IV |
| Dry Soap Noodle*** | 75.98 | 75.77 | 77.51 | 77.71 |
| TiO2 | 0.40 | 0.40 | 0.50 | 0.50 |
| Corn Starch | 20.00 | 20.00 | 20.00 | 20.00 |
| ZPT (48% active) | 0.25 | 0.46 | 0.52 | 0.52 |
| Pre-formed Zn—HEDP** | 0.40 | 0.40 | 0.40 | 0.40 |
| Perfume | — | — | 1.20 | 1.00 |
| Brightener 49 | 0.03 | 0.03 | 0.04 | 0.04 |

TABLE X-continued

| Raw Materials | Amount (w/w %) | | | |
|---|---|---|---|---|
| | I | II | III | IV |
| Tinogard TT* | 0.03 | 0.03 | 0.02 | 0.02 |
| DI water | Q.S. | Q.S. | Q.S. | Q.S. |

*Commercially available as Tinogard TT from BASF (Monheim, Germany).
**Formed by combining 19.45 w/w % $ZnSO_4$ and 25 w/w % HEDP with 55.55 w/w % DI water following the procedures described hereinabove in Example I.

***The soap noodle contained the following ingredients:

TABLE XI

| Ingredients | Wt % |
|---|---|
| Sodium palmate (from palm oil and palm oil sterine) | 49.57 |
| Sodium tallowate (from tallow) | 15.66 |
| Sodium palm kernelate (from palm kernel oil) | 14.09 |
| Unsaponifiable matter | 0.53 |
| Citric acid (anhydrous) | 0.10 |
| Sodium citrate | 0.12 |
| Pentasodium pentetate | 0.05 |
| Tetrasodium etidronate | 0.05 |
| Sodium chloride (low calcium) | 0.46 |
| Glycerine | 4.82 |
| Coconut acid | 0.95 |
| DI Water | Q.S. |

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing composition comprising:
   (a) from 0.01% to 5% by weight of zinc pyrithione (ZPT);
   (b) from 0.01% to 10% by weight of a metal-phosphonate complex comprising one or more phosphonate chelants coordinately bonded to one or more metal ions; and
   (c) from 20% to 95% by weight of at least one surfactant.

2. The personal cleansing composition of claim 1, wherein the metal in the metal-phosphonate complex is selected from the group consisting of iron, copper, and zinc.

3. The personal cleansing composition of claim 2, wherein the metal is zinc.

4. The personal cleansing composition of claim 1, which is in form of a bar soap.

5. The personal cleansing composition of claim 1, wherein the one or more phosphonate chelants each comprises one or more functional groups of the formula:

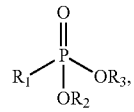

$$(I)$$

wherein $R_1$ is a linear, branched or cyclic, saturated or unsaturated, substituted or unsubstituted $C_1$-$C_{20}$ hydrocarbon group, and wherein $R_2$ and $R_3$ are independently selected from the group consisting of hydrogen and $R_1$.

6. The personal cleansing composition of claim 5, wherein said one or more phosphonate chelants are selected from the group consisting of 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra (methylene phosphonic acid) (EDTMP), diethylenetriamine penta(methylene phosphonic acid) (DTPMP), phytic acid, nitrilotrimethylene phosphonic acid (NIP), and combinations thereof.

7. The personal cleansing composition of claim 5, wherein the one or more phosphonate chelants comprise HEDP.

8. The personal cleansing composition of claim 1, having a pH value ranging from 9.9 to 10.7 when dispersed in a 1 wt % aqueous solution.

9. The personal cleansing composition of claim 8, further comprising a pH adjusting agent.

10. The personal cleansing composition of claim 9, wherein said pH adjusting agent is an acid characterized by: (1) an acid dissociation constant (pKa) of no more than 10 measured at a temperature of 25° C.; and (2) an ferric ion-complex stability constant (log K1) of no more than 8 measured at a temperature of 25° C. and an ion strength of 0.1M.

11. The personal cleansing composition of claim 10, wherein the acid is selected from the group consisting of sulfuric acid, nitric acid, phosphoric acid, lactic acid, formic acid, acrylic acid, pyruvic acid, malonic acid, glyceric acid, glycine, L-alanine, β-alanine, methylglycine, maleic acid, dihydroxytartaric acid, creatinine, asparagine, N-glycylglycine, butanoic acid, betaine, valine, N-propylglycine, 5-aminopentanoic acid, trimethylacetic acid, pentanoic acid, benzoic acid, $C_6$-$C_{22}$ fatty acids, and combinations thereof.

12. The personal cleansing composition of claim 8, which is substantially free of hydrochloric acid, citric acid, aspartic acid, picolinic acid, 4-pyridinecarboxylic acid, 3-pyridinecarboxylic acid, tartaric acid, oxalic acid, glutamic acid, or any combination thereof.

13. The personal cleansing composition of claim 1, further comprising a reducing agent.

14. The personal cleansing composition of claim 13, wherein the reducing agent is a sterically hindered phenol.

15. The personal cleansing composition of claim 14, wherein the reducing agent is pentaerythrityl tetra-di-t-butyl hydroxyhydrocinnamate.

16. The personal cleansing composition of claim 1, further comprising an inorganic zinc salt.

17. The personal cleansing composition of claim 16, wherein the inorganic zinc salt is selected from the group consisting of zinc carbonate, zinc sulfate, zinc nitrate, zinc fluoride, zinc chloride, zinc borate, and combinations thereof.

18. The personal cleansing composition of claim 17, wherein the inorganic zinc salt is zinc carbonate.

19. The personal cleansing composition of claim 1, wherein the surfactant comprises:
(a) from 0% to 95% fatty acid soap;
(b) from 0% to 50% synthetic surfactant; or
(c) mixtures thereof.

20. A bar soap composition comprising:
(a) from 0.01% to 5% by weight of ZPT;
(b) from 0.01% to 10% by weight of a Zn-HEDP complex;
(c) from 0.001% to 5% by weight of pentaerythrityl tetra-di-t-butyl hydroxyhydrocinnamate; and
(d) from 20% to 95% by weight of at least one surfactant, wherein the bar soap composition has a pH value ranging from 9.9 to 10.7 when dispersed in a 1 wt % aqueous solution.

21. A method for forming a bar soap, comprising the steps of:
(a) forming a mixture that comprises from 0.01% to 5% of ZPT, from 0.01% to 10% of a Zn-phosphonate complex comprising one or more phosphonate chelants coordinately bonded to one or more zinc ions, and from 20% to 95% of at least one surfactant by total weight of the mixture; and
(b) shaping the mixture to form a bar soap.

22. The method of claim 21, wherein the Zn-phosphonate complex is first formed by combining the phosphonate chelants with a zinc source selected from the group consisting of zinc oxide and soluble zinc salts, which is then mixed with ZPT and the surfactant.

23. The method of claim 21, wherein the Zn-phosphonate complex is formed in situ by directly combining the phosphonate chelants, a zinc source selected from the group consisting of zinc oxide and soluble zinc salts, ZPT and the surfactant.

24. The method of claim 21, wherein the mixture further comprises from 0.001% to 5% by weight of a reducing agent comprising a sterically hindered phenol.

25. The method of claim 24, wherein the reducing agent is pentaerythrityl tetra-di-t-butyl hydroxyhydrocinnamate.

* * * * *